United States Patent
Dos Santos et al.

(10) Patent No.: US 8,305,089 B2
(45) Date of Patent: Nov. 6, 2012

(54) SYSTEM FOR DETECTING, QUANTIFYING AND/OR LOCATING WATER IN AIRCRAFT SANDWICH STRUCTURES AND METHODS FOR USING THIS SYSTEM

(75) Inventors: Fernando Manuel Ferreira Dos Santos, Toulouse (FR); Jean-Louis Miane, Bordeaux (FR); Jean-Louis Arnaud, Morlanne (FR)

(73) Assignee: Airbus Operations SAS, Toulouse (FR)

( * ) Notice: Subject to any disclaimer, the term of this patent is extended or adjusted under 35 U.S.C. 154(b) by 719 days.

(21) Appl. No.: 11/721,757

(22) PCT Filed: Nov. 24, 2005

(86) PCT No.: PCT/FR2005/050989
§ 371 (c)(1),
(2), (4) Date: Dec. 3, 2009

(87) PCT Pub. No.: WO2006/072716
PCT Pub. Date: Jul. 13, 2006

(65) Prior Publication Data
US 2010/0066386 A1    Mar. 18, 2010

(30) Foreign Application Priority Data
Dec. 30, 2004 (FR) .................................. 04 53238

(51) Int. Cl.
*G01R 27/32* (2006.01)

(52) U.S. Cl. ........................................................ 324/640
(58) Field of Classification Search ................... None
See application file for complete search history.

(56) References Cited

U.S. PATENT DOCUMENTS

| | | | | |
|---|---|---|---|---|
| 3,936,736 A | * | 2/1976 | Ray | 324/642 |
| 4,097,796 A | * | 6/1978 | Lunden | 324/642 |
| 4,236,109 A | | 11/1980 | Ingle, Jr. | |
| 4,695,787 A | * | 9/1987 | Billet et al. | 324/557 |
| 5,497,100 A | * | 3/1996 | Reiser et al. | 324/643 |
| 5,686,841 A | | 11/1997 | Stolarczyk et al. | |
| 5,777,481 A | | 7/1998 | Vivekenandan | |

FOREIGN PATENT DOCUMENTS

| | | |
|---|---|---|
| DE | 19652679 C1 | 4/1998 |
| JP | 2000238154 A | 9/2000 |
| JP | 2002257752 A | 9/2002 |

OTHER PUBLICATIONS

English translation of JP 2002-257752 A Sep. 2002.*

* cited by examiner

*Primary Examiner* — Paresh Patel
(74) *Attorney, Agent, or Firm* — Perman & Green, LLP

(57) ABSTRACT

A system for the detection of water in a sandwich structure for aircraft including: a microwave generator, at least two microwaves emitters/sensors mounted in the structure, and a microwave detector capable of detecting the microwaves after propagation in the structure; a data-processing unit associated with a library containing at least one model of the structure when empty. Also methods for implementing this system as well as an aircraft including such a system.

14 Claims, 2 Drawing Sheets

SYSTEM FOR DETECTING, QUANTIFYING AND/OR LOCATING WATER IN AIRCRAFT SANDWICH STRUCTURES AND METHODS FOR USING THIS SYSTEM

This application is the National Stage of International Application No. PCT/FR2005/050989, International Filing Date, 24 Nov. 2005, which designated the United States of America, and which international application was published under PCT Article 21(2) as WO Publication No. WO 2006/072716 and which claims priority from French Application No. 0453238, filed 30 Dec. 2004.

The disclosed embodiments relate to a system and a method for detecting, quantifying and locating the presence of water in aircraft box-type structures and especially in sandwich-type composite structures. The disclosed embodiments find application in aeronautics and especially in the field of maintenance with non-destructive controls on aircraft structures. The disclosed embodiments can be applied more particularly to what are called box structures, i.e. closed structures made of sandwich-type composite materials with an external carbon envelope and an internal honeycomb layer made of cardboard, for example Nomex®, or a honeycomb structure using glass fibers.

BACKGROUND

In aeronautics and especially in the maintenance of the aircraft in service, it is important to detect the presence of water in the structures of the aircraft. Water may be present in certain parts of the aircraft, especially in parts made of sandwich-type composite material. A "sandwich"-type material is a material having a honeycomb type cellular or alveolar structure lined on each side with a skin. These skins may be made out of impermeable material. They may be shaped so as to meet on the edges of the part thus forming an envelope around the alveolar structure. These parts are said to be boxed. For example, landing gear doors or hatches, rudders, radomes or elevators are parts that are frequently made of sandwich composite material. Now, the presence of water in these parts, especially in the intermediate zone, affects the behavior and weight of the structures. This may lead to unwanted behavior on the part of the aircraft in flight. At present, the presence of water in the structures is detected either by regular inspection in the maintenance phase or by signs of its presence (swelling of structures, condensation stains, etc.) or, in extreme cases, by the effects on the mechanical actuators caused by the increase in the weight of the structures.

In certain cases, a part may be damaged, leading to the complete changing of the part. In particular, when water is detected in a sandwich-type composite part, this part must obligatorily be removed and the damage caused by this water must be repaired. To this end, the aircraft has to be immobilized for a certain time. It is moreover necessary to immobilize the aircraft to inspect these parts, prior to any repair, in order to determine the presence or absence of water. To carry out an inspection of the aircraft, it is necessary to immobilize the aircraft for a relatively lengthy period. Now, immobilizing an aircraft is costly. Furthermore, the inspection techniques used at present are also costly and often difficult to implement. The inspection of the structures of an aircraft to detect the presence of water is done by techniques of thermography or radiography for example. Thermography necessitates the heating of the entire structure and radiography necessitates the isolating of the part to be inspected. These non-destructive inspection techniques are complex, their implementation is lengthy and they require special precautions of use.

SUMMARY

The disclosed embodiments are aimed precisely at overcoming the drawbacks of the techniques explained herein. To this end, the disclosed embodiments propose a system and a method for detecting, quantifying and/or locating the presence of water in sandwich structures by means of electromagnetic microwaves generated in the structure to be inspected. This system and this method are used for the easy detection of the presence of water in the structure, enabling repairs to be made ahead of time and therefore at lower cost.

More specifically, the disclosed embodiments relate to a system for the detection of water in a sandwich structure for aircraft, comprising:
a microwave generator,
at least two microwaves emitters/sensors mounted in the structure,
a microwave detector capable of detecting the microwaves after propagation in the structure, and;
a data-processing unit associated with a library containing at least one model of the structure when empty.

This system can therefore be used to detect the presence of water in a sandwich structure and to quantify this water.

The disclosed embodiments may also comprise one or more of the following characteristics:
each emitter/sensor has a base fixed to the structure and a conductive rod situated within the structure.
the generator generates microwaves that are frequency modulated about a centre frequency chosen as a function of the structure the microwaves are modulated on a frequency interval of the order of 1 GHz about an excitation frequency of water which may depend on the structure.
the system has at least three emitters/sensors distributed in the structure to locate water by triangulation. In this way, the system of the disclosed embodiments can be used to determine the site or sites of the water point.
the generator generates pulses.
the microwave emitters/sensors are embedded in the structure while the microwave generator, the microwave detector, the data-processing unit and the library are on the ground.
the sandwich structure comprises two skins made of a material impervious to microwaves and an intermediate zone made of a low-microwave-absorbent material.
the skins are made of carbon and the intermediate zone is made of a honeycomb material, Nomex or glass fibers or a low-microwave-absorbent material such as certain synthetic foam materials.

The embodiment also relates to a method for the detection of water in an aircraft sandwich structure, comprising:
an emission of microwaves in the sandwich structure,
a reception of these microwaves by sensors after propagation in the structure,
a sequential scan at variable frequency to determine the presence of water as well as a volume of this water.

The embodiment also relates to a method of detection of water in an aircraft sandwich structure, comprising:
an emission of microwaves in the sandwich structure,
a reception of these microwaves by sensors after propagation in the structure,
a determining of the propagation times of these microwaves in the structure, and
a processing of these propagation times to deduce a location of the water therefrom.

In this case, the microwaves are emitted at a fixed frequency.

The disclosed embodiments also relate to an aircraft comprising a sandwich structure and a system as described herein.

DETAILED DESCRIPTION

The disclosed embodiments relate to a system to detect the presence of water in sandwich structures by the injection of microwaves into the structure through integrated antennas. A system of this kind is shown schematically in FIG. 1. More specifically, this FIG. 1 exemplifies a structure or part equipped with the system of the disclosed embodiments. In this example, the part 1 to be inspected is rectangular. It is clear that this part may have various shapes and, especially, shapes adapted to the structure of an aircraft. This part 1 may be, for example, the door of the front landing gear of an aircraft.

Figure 1:
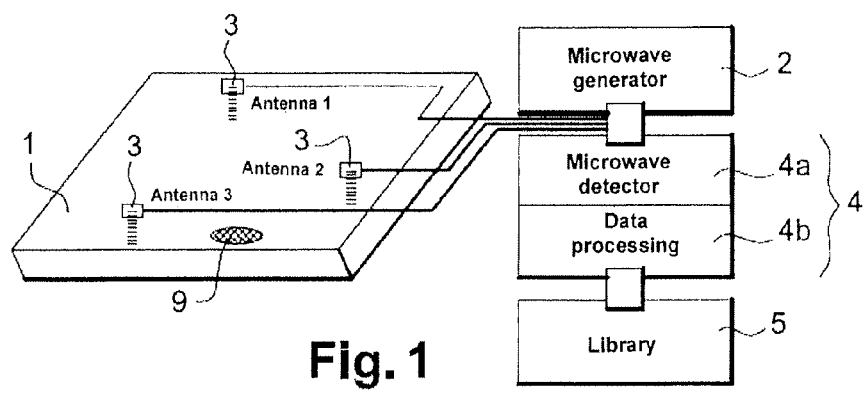
FIG. 1 is a schematic view of an example of a structure equipped with the water-detection system of the disclosed embodiments.

According to the disclosed embodiments, the system of FIG. 1 has a generator 2 of electromagnetic waves, emitters/sensors 3, a wave detector 4 constituted, for example, by a Schottky diode 4a and a data-processing unit 4b. As shall be seen herein, this data-processing unit 4b is associated with a library 5. The generator 2 produces electromagnetic waves transmitted to the interior of the part 1 by the emitters 3. The electromagnetic waves are microwaves at a frequency of the order of 2.45 GHz (depending on the shape of the structure) which may be sent in pulses or continuously (with a modulation of frequency of the order of 1 GHz).

As explained in greater detail herein, these microwaves may be emitted in the form of continuous signals or in the form of pulses.

The part 1 is made in the form of a sandwich structure having carbon skins and an intermediate zone made out of a honeycomb material, for example Nomex® or glass fibers. Carbon has the advantage of being impervious to electromagnetic waves. The honeycomb material has the advantage of not absorbing electromagnetic waves. Thus, in such a part, the waves are generated by the generator 2 and sent into the sandwich structure 1 by the emitters 3. When they are in the structure 1, the waves get propagated between the two carbon skins.

According to the disclosed embodiments, emitters/sensors 3 are mounted on the part 1. Their role is to emit and pick up the microwaves that are propagated in the intermediate zone of the part 1. A detector 4, connected to the emitters/sensors 3 by standard connection terminals, carries out the detection and processing of the information given by the microwaves. It is the processing of the propagation of these microwaves that enables the presence of water in the part 1 to be detected, located and quantified.

In the example of FIG. 1, three sensors have been represented in the part 1. As explained herein, the number of useful sensors depends on the application considered (detection and quantification or location) and on the shape of the structure to be inspected.

In the example of FIG. 1, a library 5 is associated with the data-processing unit 4b. This library 5 has a model of the part 1 when empty, i.e. a representation of the part 1 when it contains no water. The model includes the location of the different emitters/sensors 3 of the part 1. For example, the model stored in the library 5 may be a mapping of the empty part or a table of a model of the empty part. This model of an empty part is used to comparatively determine whether or not the part contains water. More specifically, at reception of the microwaves by the sensors 3, the detector 4 determines information on propagation time and shape of the waves. Then it compares this information with the data of the model recorded in the library 5. Depending on the shape of the waves, and by comparison with the model, the detector 4 determines the quantity of water in the structure and therefore the presence of a water point 9 in the structure. Furthermore, depending on the propagation time between the emitter/sensor 3 and the different obstacles or walls in the structure, and by comparison with the model, the detector 4 determines the location of this water in the structure, i.e. the site at which this water is located in the structure.

As explained herein, the sensors are fixed in the structure; they are therefore taken on board with the structure. The generator and the detector may be external devices, i.e. devices that remain on the ground and are used solely at the time of maintenance. This system is simple to implement. The parts can be inspected regularly on the ground, during the aircraft maintenance phase, thus preventing an excessively lengthy immobilization. Furthermore, the system enables the detection of water in small quantities, thus enabling the part to be repaired before it is excessively damaged. The repairing is therefore done quickly and costs little. The aircraft is immobilized for a short period.

In one variant of the disclosed embodiments, the generator and the detector are also on board the aircraft.

Figure 2:
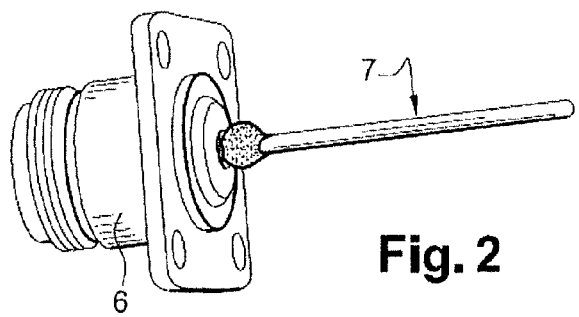
FIG. 2 is a view in perspective of an antenna of the system of the disclosed embodiments.
Figure 3:
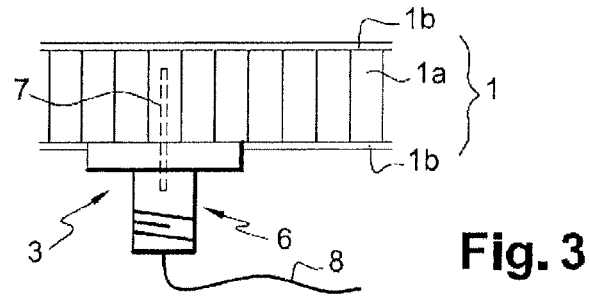
FIG. 3 is a view in section of an antenna of the system of the disclosed embodiments mounted on a sandwich structure.

One example of an emitter/sensor 3, also called an antenna, is shown in FIGS. 2 and 3. More specifically, FIG. 2 shows a view in perspective of a non-mounted antenna. FIG. 3 shows a view in section of the same antenna when it is mounted in a sandwich structure 1 that has to be inspected.

This antenna 3 has a base 6 fixed to the structure of the part 1 and a conductive rod 7 extending beyond the base 6. The conductive rod 7 is inserted into the intermediate honeycomb zone 1a. The length of this rod 7 is adapted to the structure to be controlled. This length may be of the order of 50 mm. The base 6 is fixed by one of its ends to one of the skins 1b of the part 1. The other end of the base 6 is connected, for example by a wire link 8, to the generator 2 and to the detector 4. Each antenna 3 has the role of emitting and picking up the microwaves that propagate in the intermediate zone 1a of the part 1, i.e. the zone between the carbon skins 1b.

As explained herein, the system of the disclosed embodiments can be used to detect the presence of water in a sandwich structure. It can also be used to locate and/or quantify this water.

Figure 4:
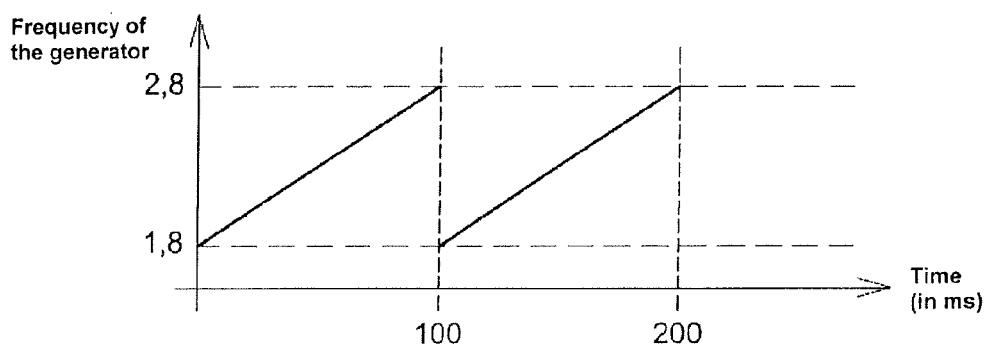
FIG. 4 represents an example of a signal generated with the system according to a first embodiment.

In a first embodiment of the disclosed embodiments, the water in the structure can be quantified by means of a scan that enables the uniformization of the absorption of the wave in the structure. The parameters of transmission and reflection of the wave are used to determine the volume of water in the structure owing to the dielectric losses that water displays at the operating frequencies of the system (for example between 2 GHz and 3 GHz). To implement this mode of operation, the generator 2 generates microwaves that are frequency-modulated on a frequency interval of the order of 1 GHz about a centre frequency to be determined as a function of the structure to be controlled. This centre frequency may be the excitation frequency of water, i.e. about 2.45 GHz. This frequency depends on the shape and the characteristics of the structure to be tested. An example of a signal generated for this mode of operation is shown in FIG. 4. More specifically, FIG. 4 gives an example of a signal emitted by the generator 2, in continuous emission with a variable frequency. In this example, the wave is generated continuously, with a modulation of amplitude that varies linearly between 1.8 GHz and 2.8 GHz.

In this embodiment, the generator 2 is connected to an antenna 3 fixed into the structure. Another antenna 3, which too is fixed into the structure, is connected to the detector 4. This detector 4 is associated with an integrator circuit having a lengthy response time that gives a mean value of the signal received on a predetermined scanning period. The output voltage of the integrator circuit is proportional to the quantity of water present in the structure.

Figure 5:
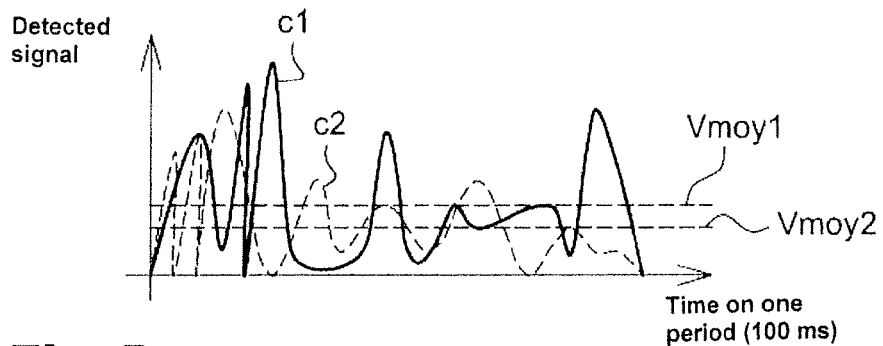
FIG. 5 represents an example of the signal detected in the absence and in the presence of water according to the first embodiment.

This embodiment with frequency variation has the advantage wherein the electrical field set up in the structure is uniform on an average. A sensor measures different values of voltage in the structure during a certain period of time and transmits the result to the processing unit 4b. Owing to the homogeneity of the electrical field, the processing unit 4b, after integration as a function of the time of the signal measured by the sensor 3, can compute the mean value of the voltage Vmoy that is characteristic of the energy propagated in the structure. One example of the mean value of the signal obtained, with and without water in the structure, is shown in FIG. 5. More specifically, the curve C1 represents the mean value of the signal in the absence of water and the curve C2 represents the mean value of the signal in the presence of water.

Without the presence of water, the mean value Vmoy1 corresponds to the mean value of the voltage of the measured signal. In the presence of water in the structure, the mean value of the voltage drops to the value Vmoy2. For, when water is excited by the microwaves, it absorbs a part of the energy emitted, thus reducing the energy restored in the form of voltage at the sensor 3. The mean value of the voltage computed by the processing unit 4b therefore reflects the presence or absence of water in the structure by comparison with a model of a waterless structure contained in the library associated with the processing unit 4b. Furthermore, the mean value of the voltage Vmoy progresses linearly as a function of the quantity of water present in the structure. Thus, the variation of voltage between the model and the tested structure makes it possible to determine the quantity of water present in said structure.

In a second embodiment, the water may be located in the structure by means of pulses emitted by the wave generator and detected by triangulation. In other words, in this embodiment, the microwave generator 2 generates microwave pulses which have the advantage of preventing the creation of standing wave modes in the sandwich structure and therefore enabling the water to be located.

Figure 6:
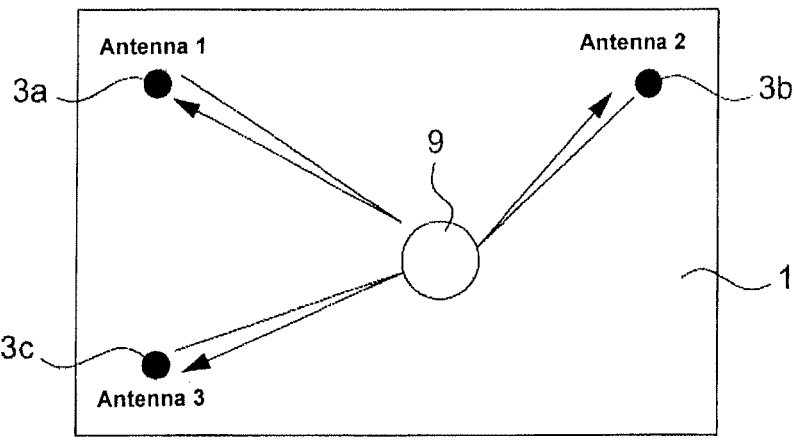
FIG. 6 represents an example of distribution of the antennas in a sandwich structure according to a second embodiment.

In this embodiment, at least three emitters/sensors are placed at distinct places in the structure. The knowledge of the propagation time and of the shapes in the structure make it possible, by triangulation, to locate the water-containing region with precision through a comparison of this information with the data from the model recorded in the library. An example of positioning of the sensors for this second embodiment is shown in FIG. 6. More specifically, this FIG. 6 is a top view representing an example of distribution of three sensors 3a, 3b and 3c in the structure 1 around a water point 9. Such a system is used to compute the propagation time of the microwaves in the structure and deduce the location of the water therefrom.

Figure 7:
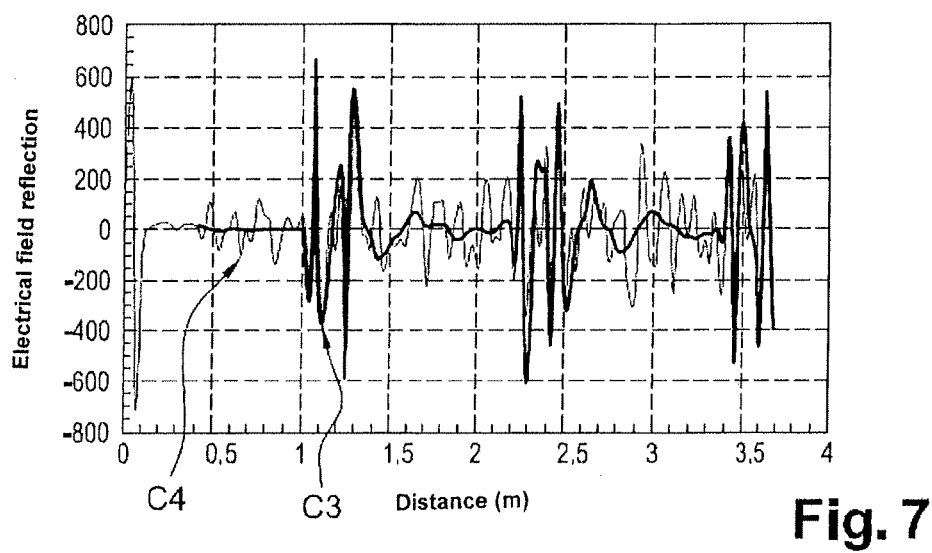
FIG. 7 represents an example of signals detected in the presence and in the absence of water in a second embodiment.

FIG. 7 exemplifies signals detected by an antenna in this second embodiment. More specifically, the curve C3 shows an example of pulses when the structure is empty of water and the curve C4 shows an example of an echo after reflection on a defect, i.e. when there is water (for example 5 ml of water).

Once the exact site of the water has been determined, the damaged region of the structure can be repaired in limiting the region of repair solely to the site of the water.

The system of the disclosed embodiments that has just been described can implement a method for detecting and quantifying water in a sandwich structure. This method comprises:
    emission of microwaves in the part 1 by means of a pulse generator 2 and emitters 3,
    reception of these microwaves which are propagated inside the part 1 by means of sensors 3 connected to the detector 4; the sensors receive microwaves that have been picked up by the other emitters of the system,
    performance of a sequential scan by the microwaves at variable frequency (triangular pulse) in the part 1.
    comparison with a model of said part memorized in the library 5 and determining of the volume of this water point and, therefore, of the presence of water in the structure.

The disclosed embodiments can implement a method of detection and location of water in a sandwich structure. This method comprises the following steps:
    emission of microwaves in the sandwich structure,
    reception of these microwaves by sensors after propagation in the structure; each sensor receives the microwaves that it has itself emitted and are reflected by the water in the structure;
    determining the propagation times of these microwaves in the structure, and
    processing these propagation times to deduce a location of the water therefrom.

In this method of locating water in the structure, the microwaves are emitted at a fixed frequency.

The two methods that have just been described may be implemented by a same system of the type described herein. They may be applied independently of each other or one after the other during a same inspection of the aircraft.

The invention claimed is:

1. A system for the detection of water in a sandwich structure for aircraft, comprising:
    a microwave generator,
    at least two microwaves emitters/sensors mounted in the structure, and
    a microwave detector capable of detecting the microwaves after propagation in the structure; and
    a data-processing unit associated with a library containing at least one model of the structure when empty.

2. The system of detection according to claim 1, wherein each emitter/sensor has a base fixed to the structure and a conductive rod situated within the structure.

3. The system of detection according to claim 1, wherein the generator generates microwaves that are frequency-modulated about a centre frequency chosen as a function of the structure.

4. The system of detection according to claim 3, wherein the microwaves are modulated on a frequency interval of the order of 1 GHz about an excitation frequency of water.

5. The system of detection according to claim 1, wherein the system has at least three emitters/sensors distributed in the structure to locate water by triangulation.

6. The system of detection according to claim 5, wherein the generator generates pulses.

7. The system according to claim 1, wherein:
the microwave emitters/sensors are embedded in the structure,
the microwave generator, the microwave detector, the data-processing unit and the library are on the ground.

8. The system of detection according to claim 1, wherein sandwich structure comprises two skins made of a material impervious to microwaves and an intermediate zone made of a low-microwave-absorbent material.

9. The system of detection according to claim 8, wherein the skins are made of carbon and the intermediate zone is made of a honeycomb material, Nomex® or glass fiber or a low-microwave-absorbent material such as certain synthetic foam materials.

10. A method for the detection of water in an aircraft sandwich structure, comprising:
an emission of microwaves in the sandwich structure,
a reception of these microwaves by sensors after propagation in the structure, and
a processing of these propagation times to deduce a location of the water therefrom.

11. The method for the detection of water according to claim 10, wherein the processing comprises a sequential scan at variable frequency to determine the presence of water as well as a volume of this water.

12. The method for the detection of water according to claim 10, wherein the processing comprises:
a determining of the propagation times of these microwaves in the structure, and
a processing of these propagation times to deduce a location of the water therefrom.

13. The method according to claim 12 wherein that the microwaves are emitted at a fixed frequency.

14. An aircraft comprising:
a sandwich structure; and
a system for the detection of water in a sandwich structure for aircraft, including:
a microwave generator,
at least two microwaves emitters/sensors mounted in the structure, and
a microwave detector capable of detecting the microwaves after propagation in the structure; and
a data-processing unit associated with a library containing at least one model of the structure when empty.

* * * * *